(12) United States Patent
Inagaki et al.

(10) Patent No.: US 11,766,778 B2
(45) Date of Patent: Sep. 26, 2023

(54) DRIVING DEVICE AND METHOD FOR CONTROLLING THE SAME, AND PARALLEL LINK ROBOT AND METHOD FOR CONTROLLING THE SAME

(71) Applicant: NSK LTD., Tokyo (JP)

(72) Inventors: Satoshi Inagaki, Kanagawa (JP); Sumio Sugita, Kanagawa (JP)

(73) Assignee: NSK LTD., Tokyo (JP)

( * ) Notice: Subject to any disclaimer, the term of this patent is extended or adjusted under 35 U.S.C. 154(b) by 0 days.

(21) Appl. No.: 17/921,173

(22) PCT Filed: Dec. 2, 2021

(86) PCT No.: PCT/JP2021/044324
§ 371 (c)(1),
(2) Date: Oct. 25, 2022

(87) PCT Pub. No.: WO2023/002642
PCT Pub. Date: Jan. 26, 2023

(65) Prior Publication Data
US 2023/0122978 A1 Apr. 20, 2023

(30) Foreign Application Priority Data

Jul. 19, 2021 (JP) ................................. 2021-118751

(51) Int. Cl.
*B25J 9/16* (2006.01)
*B25J 15/00* (2006.01)
(Continued)

(52) U.S. Cl.
CPC ............... *B25J 9/163* (2013.01); *A61B 34/30* (2016.02); *A61F 9/007* (2013.01); *B25J 9/1692* (2013.01);
(Continued)

(58) Field of Classification Search
CPC ........ B25J 9/163; B25J 9/1692; B25J 13/088; B25J 15/0019; B25J 9/123; B25J 9/0042;
(Continued)

(56) References Cited

U.S. PATENT DOCUMENTS 6,723,106 B1 * 4/2004 Charles ................. B25J 9/1065
606/130
10,663,942 B2 5/2020 Kondou et al.
(Continued)

FOREIGN PATENT DOCUMENTS

EP 1 189 331 A1 3/2002
JP 11-010575 A 1/1999
(Continued)

OTHER PUBLICATIONS

Japanese Decision to Grant a Patent of No. 2022-516459 (Priority JP2021-118751) dated May 10, 2022.
(Continued)

*Primary Examiner* — Abby Y Lin
*Assistant Examiner* — Esvinder Singh
(74) *Attorney, Agent, or Firm* — Sughrue Mion, PLLC

(57) ABSTRACT

A driving device includes a corrector, an actuator, and a position sensor. The actuator includes a nut connected to a movable part, a ball screw shaft onto which the nut is screwed, and a pulse motor that drives to rotate the ball screw shaft. The corrector includes a correction amount map in which a position correction amount for calibrating a predictable error is mapped for each position of the movable part. The corrector estimates an ideal movement position to which the movable part moves based on a command signal and refers to the correction amount map to calculate the position correction amount corresponding to a present position detected by the position sensor. The corrector generates a correction signal by correcting the command signal so as to reduce the difference between a corrected present position obtained by correcting the present position by the position correction amount and the ideal movement position.

4 Claims, 12 Drawing Sheets

(51) Int. Cl.
*A61F 9/007* (2006.01)
*A61B 34/30* (2016.01)
*B25J 13/08* (2006.01)

(52) U.S. Cl.
CPC ......... *B25J 13/088* (2013.01); *B25J 15/0019* (2013.01); *A61B 2034/304* (2016.02)

(58) Field of Classification Search
CPC ...... B25J 9/1623; B25J 9/1602; B25J 9/1628; B25J 9/1641; B25J 9/1653; B25J 9/1674; B25J 17/0216; A61B 34/30; A61B 2034/304; A61B 2017/00398; A61F 9/007; G05B 2219/37019; G05B 2219/41326; G05B 2219/40596; G05B 19/404; G05B 2219/50047; G05B 2219/33133
See application file for complete search history.

(56) References Cited

U.S. PATENT DOCUMENTS

| 10,754,305 | B2* | 8/2020 | Iwase | B25J 9/1623 |
| 2010/0331858 | A1 | 12/2010 | Simaan et al. | |
| 2018/0299267 | A1* | 10/2018 | Durand | G05B 19/31 |
| 2019/0255708 | A1* | 8/2019 | Fujita | B25J 19/023 |
| 2020/0180154 | A1* | 6/2020 | Tsuboi | B25J 9/10 |
| 2022/0161439 | A1* | 5/2022 | Izumi | B25J 9/1692 |

FOREIGN PATENT DOCUMENTS

| JP | 2006-266999 A | 10/2006 |
| JP | 2010-058171 A | 3/2010 |
| JP | 2019-028782 A | 2/2019 |
| WO | 01/63730 A1 | 8/2001 |

OTHER PUBLICATIONS

International Search Report of PCT/JP2021/044324 dated Feb. 8, 2022 [PCT/ISA/210].

* cited by examiner

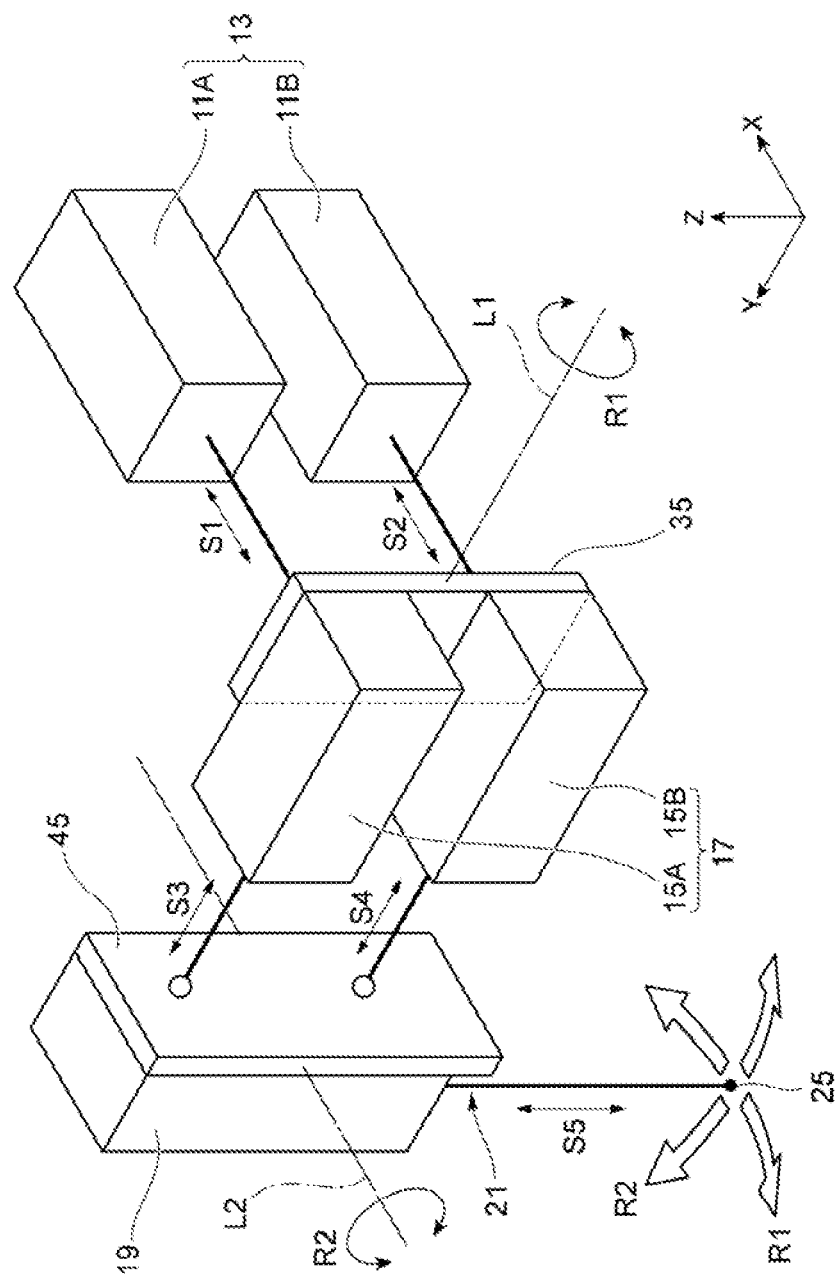

DRIVING DEVICE AND METHOD FOR CONTROLLING THE SAME, AND PARALLEL LINK ROBOT AND METHOD FOR CONTROLLING THE SAME

CROSS-REFERENCE TO RELATED APPLICATION

This application is a National Stage of PCT international application Ser. No. PCT/JP2021/044324 filed on Dec. 2, 2021 which designates the United States, incorporated herein by reference, and which is based upon and claims the benefit of priority from Japanese Patent Application No. 2021-118751 filed on Jul. 19, 2021, the entire contents of which are incorporated herein by reference.

FIELD

The present disclosure relates to a driving device and a method for controlling the same, and a parallel link robot and a method for controlling the same.

BACKGROUND

Robots with parallel links have the advantage of having higher positioning accuracy and higher rigidity than typical serial link robots. Positioning errors of shafts constituting a robot, however, have a large effect on the accuracy in position of the distal end of the robot arm. To address this, technologies for reducing such positioning errors have been developed. Widely known is a technology for correcting positioning errors of a movable part due to friction, backlash, or other causes when the movable part is moved using a ball screw device that converts rotation of a motor into a linear motion, for example (Patent Literatures 1 and 2).

CITATION LIST

Patent Literature

Patent Literature 1: Japanese Patent Application Laid-open No. 2019-28782
Patent Literature 2: Japanese Patent Application Laid-open No. H11-10575

Technical Problem

Patent Literature 1 describes a technology for correcting position errors occurring when a movable part of a machine tool reverses its movement direction. The technology, however, does not consider the effects of lead errors of ball screws and cogging that is unique to pulse motors. If such errors are corrected by feedback control, it is necessary to increase the gain, which may possibly make the system unstable. The configuration described in Patent Literature 1 employs not a parallel link mechanism but a driving mechanism including a servo motor and a rotary encoder. It is difficult for a servo motor to maintain accurate positioning of a movable part because it has low stability when stationary. In addition, the technology uses a linear encoder besides the rotary encoder, thereby complicating the system configuration. While the technology described in Patent Literature 2 is a parallel link mechanism, it simply performs feedback control on each link. Therefore, it is difficult to accurately position the distal end of an end effector while being affected by the lead errors and the errors due to cogging described above.

Surgical robots have recently been developed to reduce burdens on doctors and patients in surgical operations. Especially in ophthalmic surgeries, such a surgical robot is used to insert a needle into the retina or other parts and is required to perform accurate position control on the needle tip in micrometer order. If the parallel link mechanism described above is used for the surgical robot, it requires high absolute accuracy and stability of each shaft.

For the foregoing reasons, there is a need for a driving device and a method for controlling the same, and a parallel link robot and a method for controlling the same that can accurately and stably control the position of the distal end of an end effector with a smaller correction amount in feedback control without complicating the structure.

SUMMARY (1) A driving device comprising a corrector configured to correct a command signal that is input and generate a correction signal, an actuator configured to move a movable part forward and backward based on the correction signal, and a position sensor configured to detect a present position of the movable part, wherein the actuator comprises a nut connected to the movable part, a ball screw shaft onto which the nut is screwed, and a pulse motor configured to drive to rotate the ball screw shaft, the corrector includes a correction amount map in which a position correction amount for calibrating a predictable error due to a structure of the actuator is mapped for each position of the movable part, the corrector estimates an ideal movement position to which the movable part moves based on the command signal, the corrector refers to the correction amount map and calculates the position correction amount corresponding to the present position detected by the position sensor, and the corrector generates the correction signal by correcting the command signal so as to reduce a difference between a corrected present position obtained by correcting the present position by the position correction amount and the ideal movement position.

(2) A method for controlling a driving device comprising a corrector configured to correct a command signal that is input and generate a correction signal, an actuator configured to move a movable part forward and backward based on the correction signal, and a position sensor configured to detect a present position of the movable part, wherein the actuator comprises a nut connected to the movable part, a ball screw shaft onto which the nut is screwed, and a pulse motor configured to drive to rotate the ball screw shaft, the corrector includes a correction amount map in which a position correction amount for calibrating a predictable error due to a structure of the actuator is mapped for each position of the movable part, and the method comprises: estimating an ideal movement position to which the movable part moves based on the command signal; referring to the correction amount map and calculating the position correction amount corresponding to the present position detected by the position sensor; and generating the correction signal by correcting the command signal so as to reduce a difference between a corrected present position obtained by correcting the present position by the position correction amount and the ideal movement position.

(3) A parallel link robot comprising a plurality of driving devices each comprising a corrector configured to correct a command signal that is input and generate a correction signal, an actuator configured to move a movable part forward and backward based on the correction signal, and a position sensor configured to detect a present position of the movable part, the parallel link robot being configured to change a position and a posture of a robot distal end shaft, wherein the actuator comprises a nut connected to the movable part, a ball screw shaft onto which the nut is screwed, and a pulse motor configured to drive to rotate the ball screw shaft, the corrector includes a correction amount map in which a position correction amount for calibrating a predictable error due to a structure of the actuator is mapped for each position of the movable part, the corrector estimates an ideal movement position to which the movable part moves based on the command signal, the corrector refers to the correction amount map and calculates the position correction amount corresponding to the present position detected by the position sensor, and the corrector generates the correction signal by correcting the command signal so as to reduce a difference between a corrected present position obtained by correcting the present position by the position correction amount and the ideal movement position.

(4) A method for controlling a parallel link robot comprising a plurality of driving devices each comprising a corrector configured to correct a command signal that is input and generate a correction signal, an actuator configured to move a movable part forward and backward based on the correction signal, and a position sensor configured to detect a present position of the movable part, the parallel link robot being configured to change a position and a posture of a robot distal end shaft, wherein the actuator comprises a nut connected to the movable part, a ball screw shaft onto which the nut is screwed, and a pulse motor configured to drive to rotate the ball screw shaft, the corrector includes a correction amount map in which a position correction amount for calibrating a predictable error due to a structure of the actuator is mapped for each position of the movable part, and the method comprises: estimating an ideal movement position to which the movable part moves based on the command signal; referring to the correction amount map and calculating the position correction amount corresponding to the present position detected by the position sensor; and generating the correction signal by correcting the command signal so as to reduce a difference between a corrected present position obtained by correcting the present position by the position correction amount and the ideal movement position.

Advantageous Effects of Invention

The present disclosure can accurately and stably control the position of the distal end of an end effector with a smaller correction amount in feedback control without complicating the structure.

BRIEF DESCRIPTION OF DRAWINGS

FIG. 4 is an explanatory view schematically illustrating the configuration and operations of the parallel link robot.

DESCRIPTION OF EMBODIMENTS

Embodiments according to the present invention are described below in detail with reference to the drawings. While the present embodiment describes a configuration example in which a plurality of driving devices that move a movable part forward and backward are used for a parallel link robot for ophthalmic surgery, the application example of the driving devices is not limited thereto. The use of the parallel link robot is not limited thereto.

<Configuration of the Parallel Link Robot>

Figure 1:
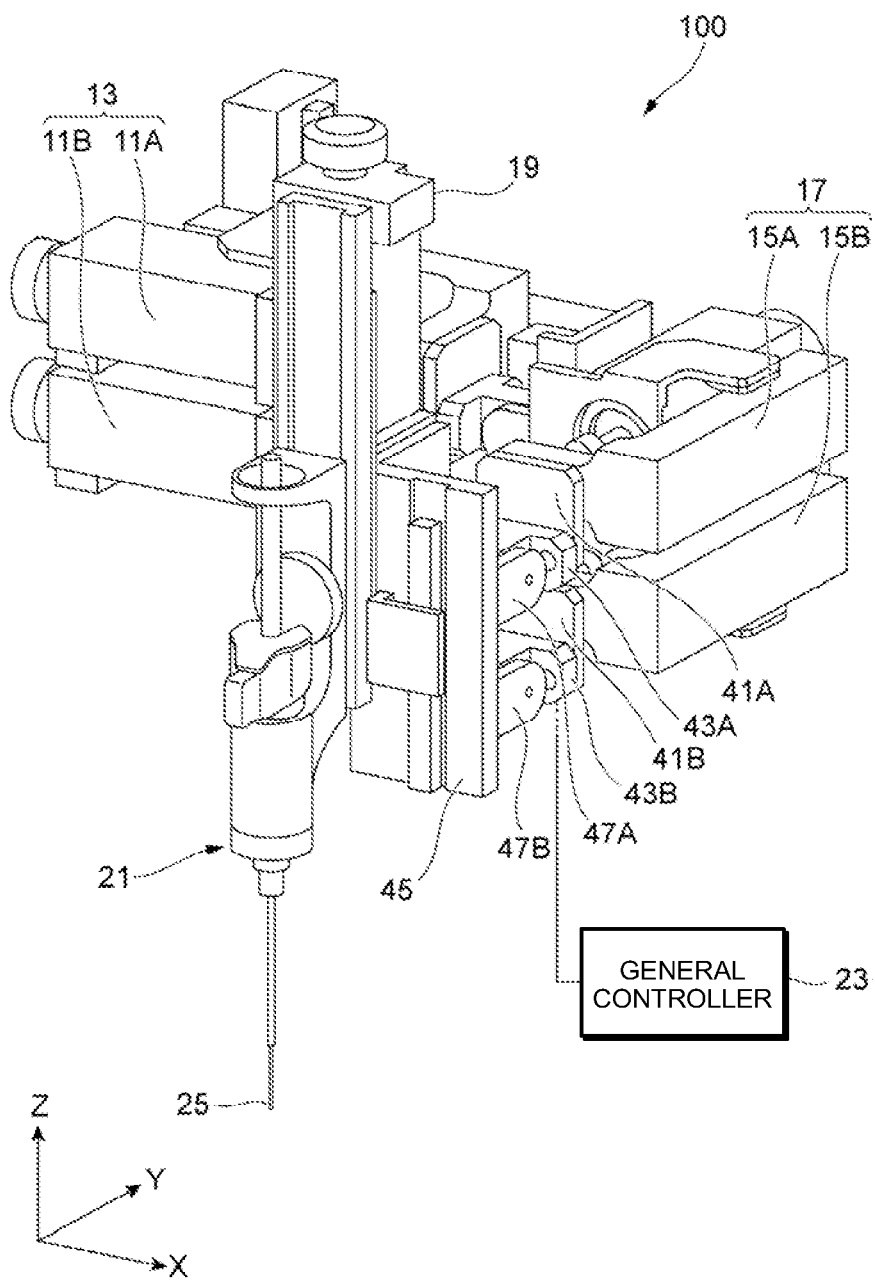
FIG. 1 is a front perspective view of a parallel link robot.
Figure 2:
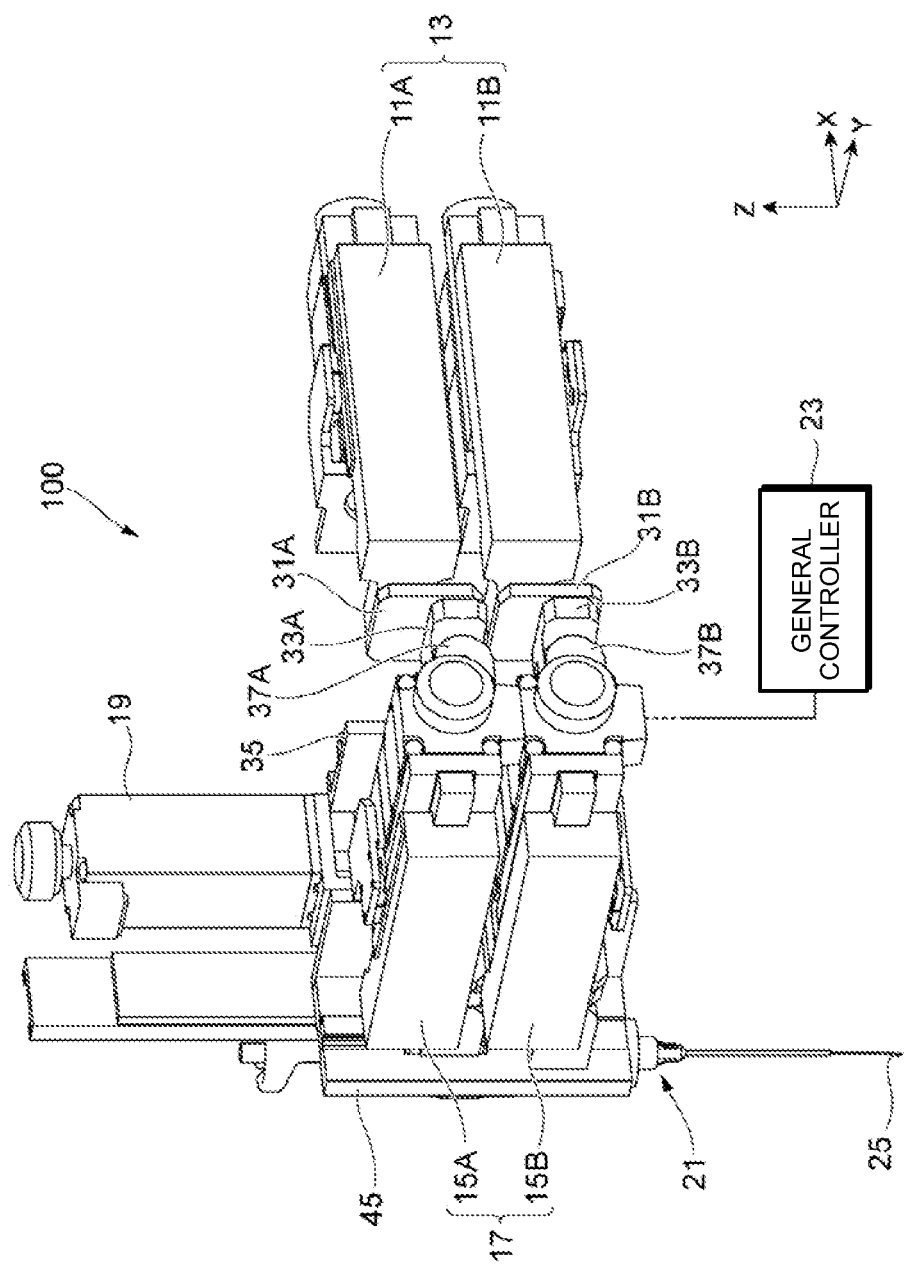
FIG. 2 is a back perspective view of the parallel link robot.

FIG. 1 is a front perspective view of a parallel link robot. FIG. 2 is a back perspective view of the parallel link robot. As illustrated in FIG. 1, a parallel link robot 100 includes a first linkage 13, a second linkage 17, a fifth driving device 19, an end effector 21 for ophthalmic surgery, and a general controller 23. The first linkage 13 includes a first driving device 11A and a second driving device 11B. The second linkage 17 includes a third driving device 15A and a fourth driving device 15B. The end effector 21 is provided to the fifth driving device 19. The end effector 21 is provided with a needle (e.g., a surgical instrument, such as a cannula) 25 at the distal end and is driven forward and backward by the fifth driving device 19.

As illustrated in FIG. 2, the first driving device 11A of the first linkage 13 moves a support plate 31A serving as movable part forward and backward with respect to the second linkage 17. Similarly, the second driving device 11B drives a support plate 31B serving as a movable part forward and backward with respect to the second linkage 17. Supports 33A and 33B are fixed to the support plates 31A and 31B, respectively.

A first connection member 35 is disposed facing the support plates 31A and 31B. Brackets 37A and 37B are fixed to the surface of the first connection member 35 facing the first linkage 13. The bracket 37A is rotatably connected to the support 33A of the support plate 31A, and the bracket 37B is rotatably connected to the support 33B of the support plate 31B.

The third driving device 15A and the fourth driving device 15B of the second linkage 17 are fixed to the surface of the first connection member 35 opposite to the surface facing the first linkage 13. As illustrated in FIG. 1, the third driving device 15A of the second linkage 17 moves a support plate 41A serving as a movable part forward and backward. Similarly, the fourth driving device 15B moves a support plate 41B serving as a movable part forward and backward. Supports 43A and 43B are fixed to the support plates 41A and 41B, respectively.

A second connection member 45 is disposed facing the support plates 41A and 41B. The second connection member 45 is a member with an L-shape in cross-section, and brackets 47A and 47B are fixed to the surface of the second connection member 45 facing the second linkage 17. The bracket 47A is rotatably connected to the support 43A of the support plate 41A, and the bracket 47B is rotatably connected to the support 43B of the support plate 41B. In the second connection member 45, the brackets 47A and 47B are fixed to one surface of the L-shaped section, and the fifth driving device 19 is fixed to the other surface thereof.

Figure 3:
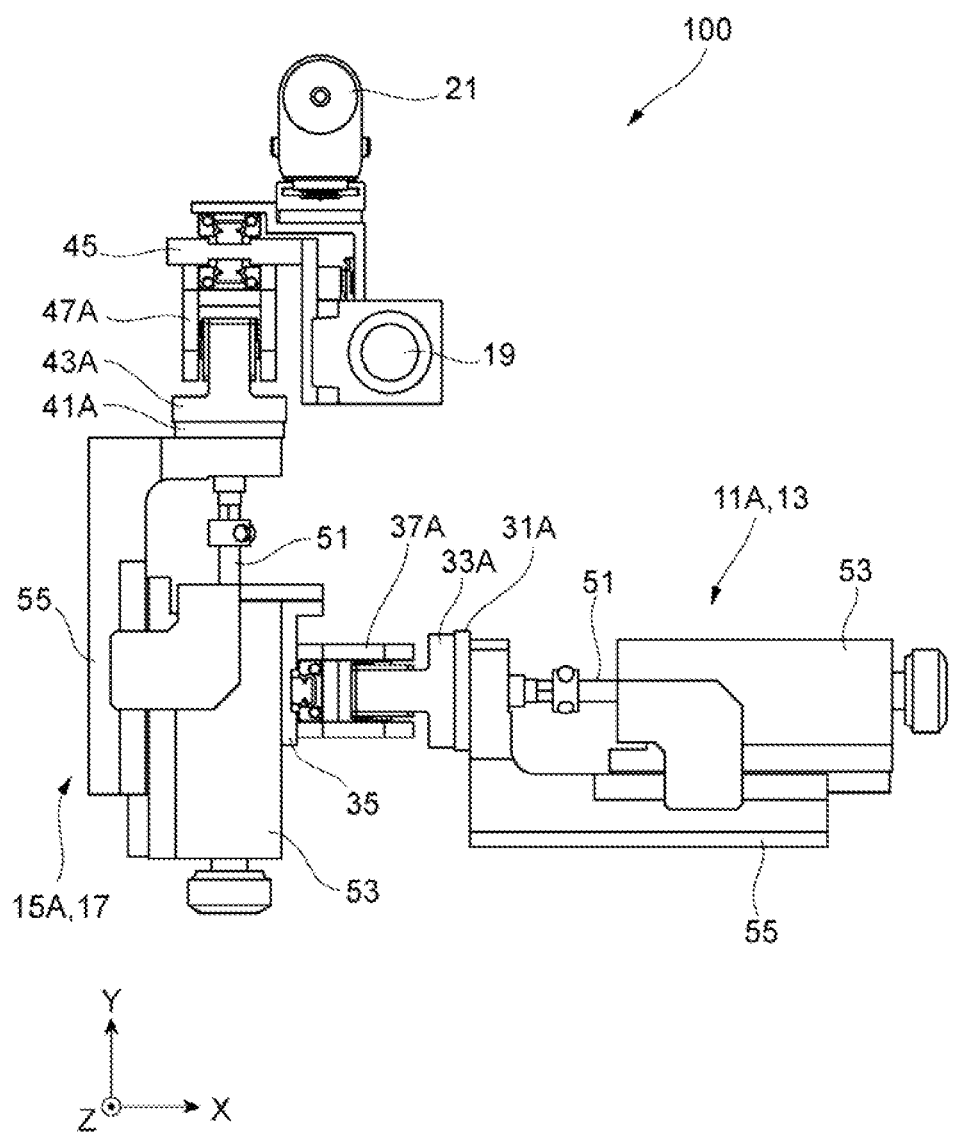
FIG. 3 is a top view of the parallel link robot.

FIG. 3 is a top view of the parallel link robot 100. The direction of movement of the movable part of the first linkage 13 is an X-direction, the direction of movement of the movable part of the second linkage 17 is a Y-direction, and the direction perpendicular to the X- and Y-directions is a Z-direction. As used herein, the direction of movement of the first linkage 13 is the horizontal direction, and the Z-direction is the vertical direction.

The first driving device 11A includes an actuator 53 and a slider 55. The actuator 53 drives a rod 51 forward and backward. The slider 55 slidably supports the actuator 53 in a uniaxial direction. The support plate 31A is fixed to part of the slider 55. Although not illustrated in the figure, the second driving device 11B has the same configuration.

The parallel link robot 100 is operated by the actuators 53 of the first driving device 11A and the second driving device 11B. In other words, in the first driving device 11A, the actuator 53 is fixed to a fixing part, which is not illustrated, and the slider 55 and the rod 51 slide in the X-direction with respect to the actuator 53 to serve as the movable part together with the support plate 31A. Although not illustrated in the figure, the second driving device 11B has the same configuration. The third driving device 15A and the fourth driving device 15B also have the same configuration except that the actuator 53 is fixed to the first connection member 35.

FIG. 4 is an explanatory view schematically illustrating the configuration and operations of the parallel link robot 100. Drive in an S1 direction by the first driving device 11A or drive in an S2 direction by the second driving device 11B causes the first connection member 35 to tilt around an axis L1 (direction of arrow R1). Drive in an S3 direction by the third driving device 15A or drive in an S4 direction by the fourth driving device 15B causes the second connection member 45 to tilt around an axis L2 (direction of arrow R2). As a result, the needle 25 at the distal end of the end effector 21 attached to the second connection member 45 with the fifth driving device 19 interposed therebetween can be moved in R1 and R2 directions. By combining drive in an S5 direction by the fifth driving device 19, the needle 25 can be moved in any desired direction in three dimensions.

In other words, in the parallel link robot 100, a pair of the first driving device 11A and the second driving device 11B and a pair of the third driving device 15A and the fourth driving device 15B enable the distal end of the end effector 21 to move. The fifth driving device 19 enables the distal end of the end effector 21 to move forward and backward along the axial direction. Thus, the parallel link robot 100 can stably control the end effector with a simple configuration. In addition, the parallel link robot 100 can perform highly accurate and independent position control by individual operations of the driving devices and finely control the distal end of the end effector 21.

Figure 5A:
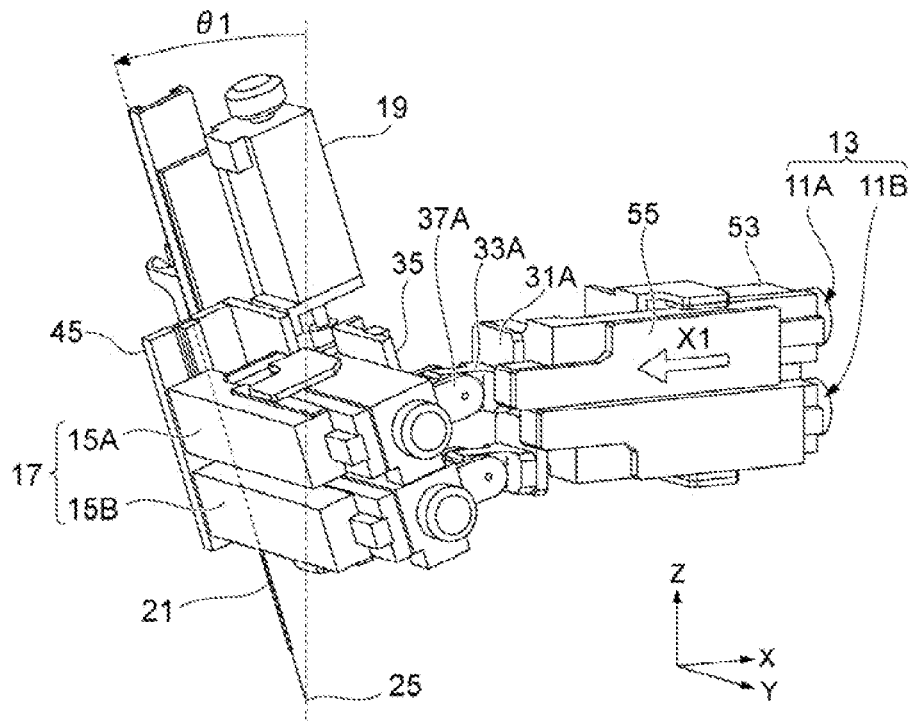
FIG. 5A is a view of movement of a needle 25 when a first linkage 13 is driven.
Figure 5B:
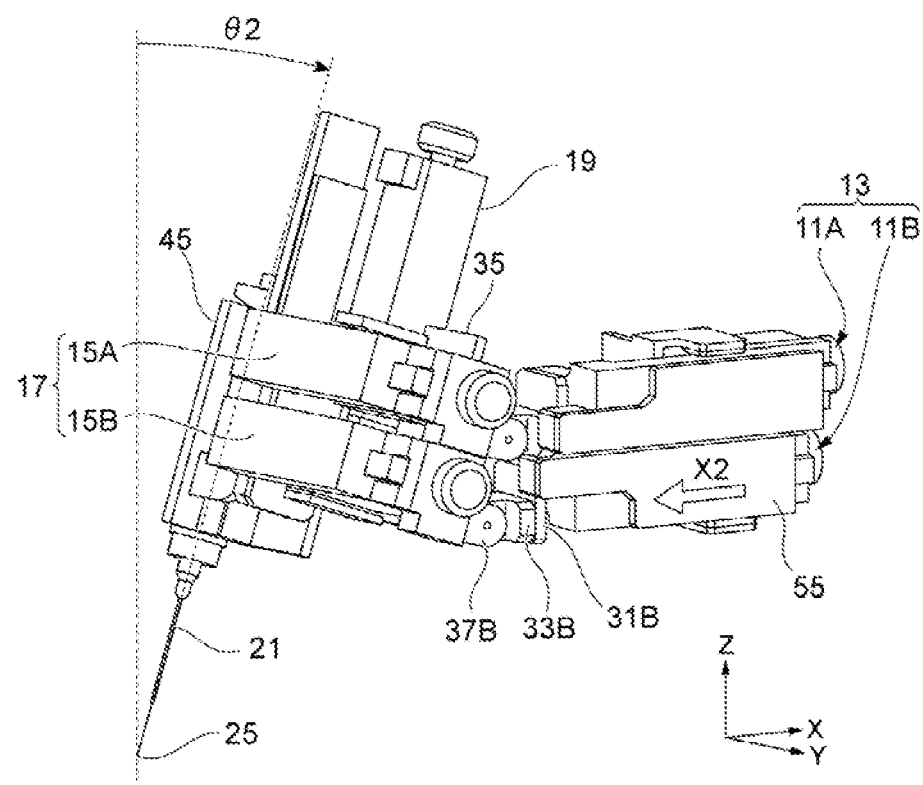
FIG. 5B is a view of movement of the needle 25 when the first linkage 13 is driven in a direction opposite to the direction illustrated in FIG. 5A.

FIG. 5A is a view of movement of the needle 25 when the first linkage 13 is driven. FIG. 5B is a view of movement of the needle 25 when the first linkage 13 is driven in a direction opposite to the direction illustrated in FIG. 5A. As illustrated in FIG. 5A, when the first driving device 11A of the first linkage 13 is driven in the direction of arrow X1, the first connection member 35 tilts, and the second linkage 17, the fifth driving device 19, and the end effector 21 fixed to the first connection member 35 also tilt. As illustrated in FIG. 5B, when the second driving device 11B of the first linkage 13 is driven in the direction of arrow X2, the first connection member 35 tilts in a direction opposite to the direction illustrated in FIG. 5A, and the second linkage 17, the fifth driving device 19, and the end effector 21 also tilt.

With this operation, the end effector 21 can swing at angles θ1 and θ2 with respect to the vertical direction around the tip position of the needle 25, for example. The center of swing can be appropriately adjusted by extending the needle 25 by the fifth driving device 19.

The parallel link robot 100 with the present configuration can perform a highly accurate operation in micrometer order in five to six degrees of freedom. Therefore, the parallel link robot 100 can be used for a robot for ophthalmic surgery that requires what is called remote center of motion (RCM) control for causing the robot to move around a specific point at a remote position from the actuator.

<Position Error due to Drive of the Actuator>

Figure 6:
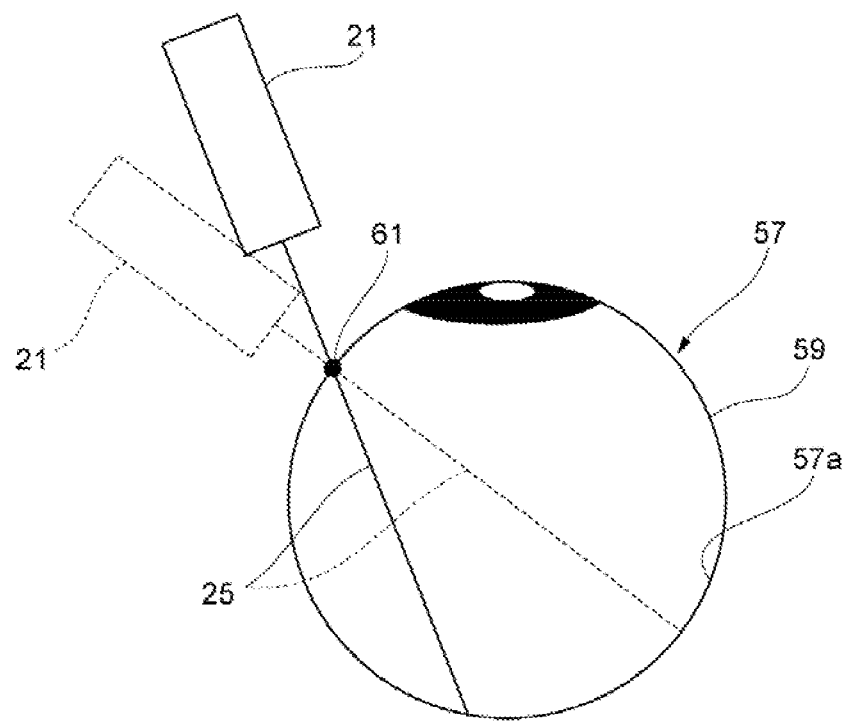
FIG. 6 is an explanatory view schematically illustrating an example of control on an end effector in ophthalmic surgery.

FIG. 6 is an explanatory view schematically illustrating an example of control on the end effector in ophthalmic surgery. To form a hole in a sclera 59 of an eyeball 57, insert the needle 25 into the eyeball through the hole, and give treatment to part of an eyeground 57a, for example, the needle 25 is controlled using an entrance 61 into the eyeball as the center of rotation. In such a case, high accuracy in positioning each shaft by the actuator is required. In addition, maintaining the posture of the end effector 21 during surgery is very important, and each shaft needs to stably maintain its position.

Figure 7:
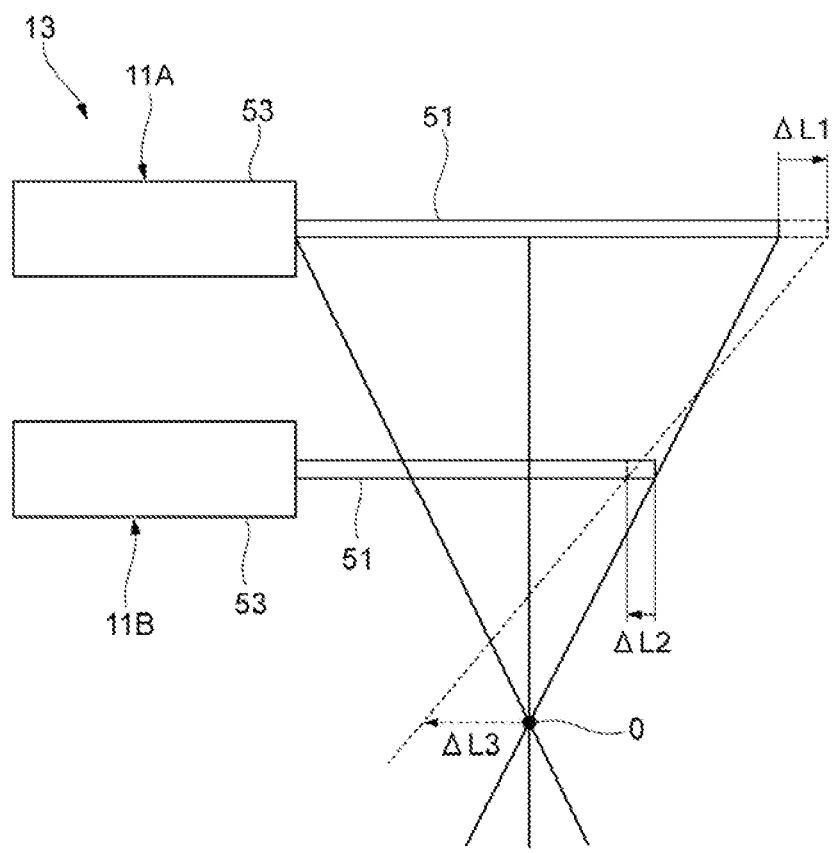
FIG. 7 is a view for explaining the effect of errors of actuators using the first linkage as an example.

FIG. 7 is a view for explaining the effect of errors of the actuators using the first linkage 13 as an example. The drive operations of the first driving device 11A and the second driving device 11B determine the tilt angles θ1 and θ2 of the first connection member 35 (refer to FIG. 5), and the position and the posture of the needle 25 are determined based on the tilt angles. If an error ΔL1 occurs in the actuator 53 of the first driving device 11A, and an error ΔL2 occurs in the actuator 53 of the second driving device 11B, the tilt angle of the first connection member 35 significantly changes if the magnitudes of the errors ΔL1 and ΔL2 are minute. This angular variation results in an error ΔL3 at a position O, and the error increases with distance from the actuators 53.

To address this, the parallel link robot 100 with the present configuration independently controls the actuators 53 of the first linkage 13, the second linkage 17, and the fifth driving device 19 to prevent occurrence of position errors.

<Control of the Actuator>

The following describes control on each actuator 53. The first driving device 11A, the second driving device 11B, the third driving device 15A, the fourth driving device 15B, and the fifth driving device 19 have the same configuration and are collectively referred to as a driving device 10 in the following description.

Figure 8:
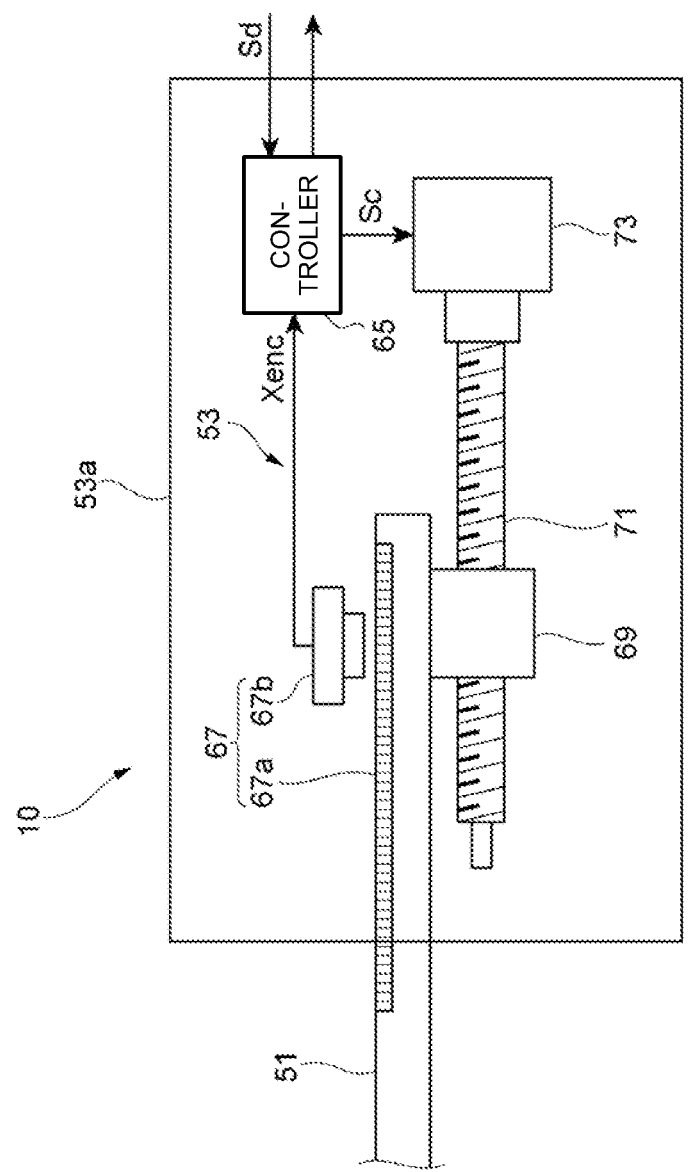
FIG. 8 is a diagram of a schematic configuration of a driving device.

FIG. 8 is a diagram of a schematic configuration of the driving device 10. The driving device 10 includes a controller 65, the actuator 53, and a position sensor 67. The controller 65 corrects input command signals Sd to generate correction signals Sc. The actuator 53 moves the rod 51 serving as a movable part forward and backward based on the correction signals Sc. The position sensor 67 detects the present position of the rod 51 serving as a movable part. The position sensor 67 is a linear encoder including a scale 67a and a reader 67b. The use of a linear encoder enables the position sensor 67 to directly detect movement of the movable part along the direction of movement and can perform highly accurate detection. The controller 65 and the position sensor 67 may be disposed in a housing 53a of the actuator 53 or near the housing 53a.

The actuator 53 includes a nut 69, a ball screw shaft 71, and a pulse motor 73. The nut 69 is connected to the rod 51. The ball screw shaft 71 is a shaft onto which the nut 69 is screwed. The pulse motor 73 drives to rotate the ball screw shaft 71. In FIG. 8, the ball screw shaft 71 is rotatably supported, and the nut 69 moves. Alternatively, the nut may be rotatably fixed to the pulse motor, and the ball screw shaft may be moved. In this case, the actuator can be made more compact.

The pulse motor 73 is preferably a stepping motor. A stepping motor has higher stability when it is stationary than a servomotor has, and the use of the stepping motor can simplify the configuration because it is not necessary to provide a rotary encoder for detecting rotation of a servomotor. Compared with a piezoelectric actuator, the stepping motor can be driven by low voltage suitable for medical equipment. Compared with a shaft motor, the stepping motor can maintain a stationary state by frictional force between the ball screw shaft 71 and the nut 69 when the power supply is turned off and can stably maintain the posture of the robot.

Figure 9:
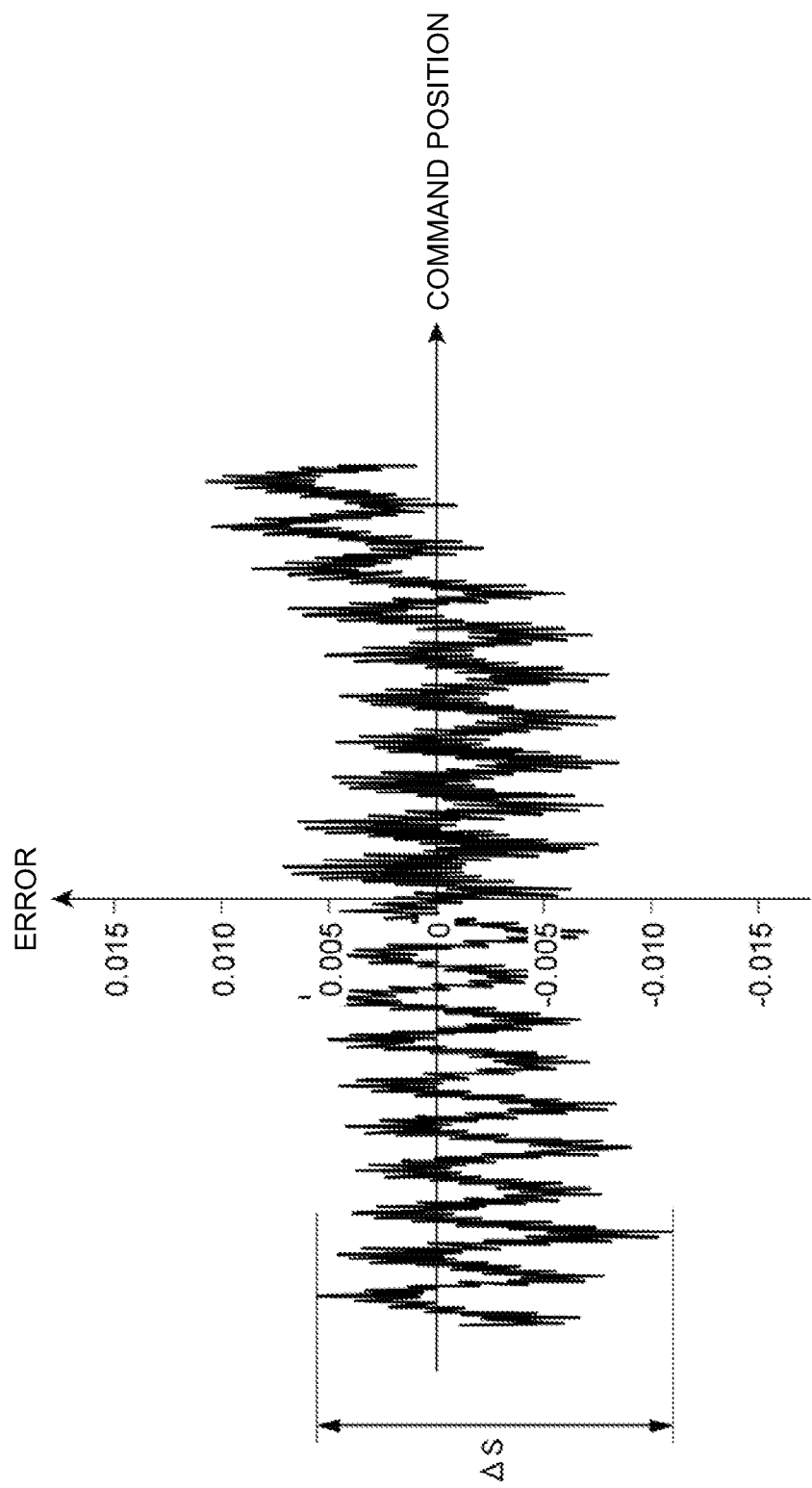
FIG. 9 is a graph illustrating errors between a command position given to the actuator and an actual movement position for each command position.

The pulse motor 73, however, has a position error due to cogging, and the ball screw device including the ball screw shaft 71 and the nut 69 has a lead error. FIG. 9 is a graph illustrating errors between a command position given to the actuator and an actual movement position for each command position. The errors indicating variations between the command position and the actual movement position illustrated in FIG. 9 are caused by lead errors of several micromillimeters to ten and several micrometers of the ball screw device occurring per motor revolution and by a vibration of several micrometers generated several tens to hundreds of times per motor revolution due to cogging of the pulse motor 73. In the case illustrated in FIG. 9, errors $\Delta S$ of approximately 20 μm occur.

The lead error of the ball screw device and the error due to cogging of the pulse motor are errors that can be measured in advance. These errors can be corrected by constructing, prior to control, a correction amount map obtained by mapping the position correction amount for calibrating the error with respect to the movement position of the movable part due to driving of the actuator. By contrast, errors caused by thermal expansion, abrasion, or the like of the ball screw device cannot be measured in advance.

<First Control Method>

A first control method of the parallel link robot 100 divides errors into errors measurable in advance and errors unmeasurable in advance and corrects commands to the actuator. In other words, information on a target position indicated by the command signals is corrected as follows: the errors measurable in advance are corrected by referring to the correction amount map resulting from mapping to obtain a position correction value corresponding to positional information obtained from the position sensor 67 and performing feedforward control; and the errors unmeasurable in advance are corrected by performing feedback control.

The pulse motor 73 included in the actuator 53 illustrated in FIG. 8 is driven by the correction signals Sc including a speed correction value Vc obtained by correcting a speed setting value Vdes of the command signals Sd input to the driving device 10 by a predetermined procedure.

Figure 10:
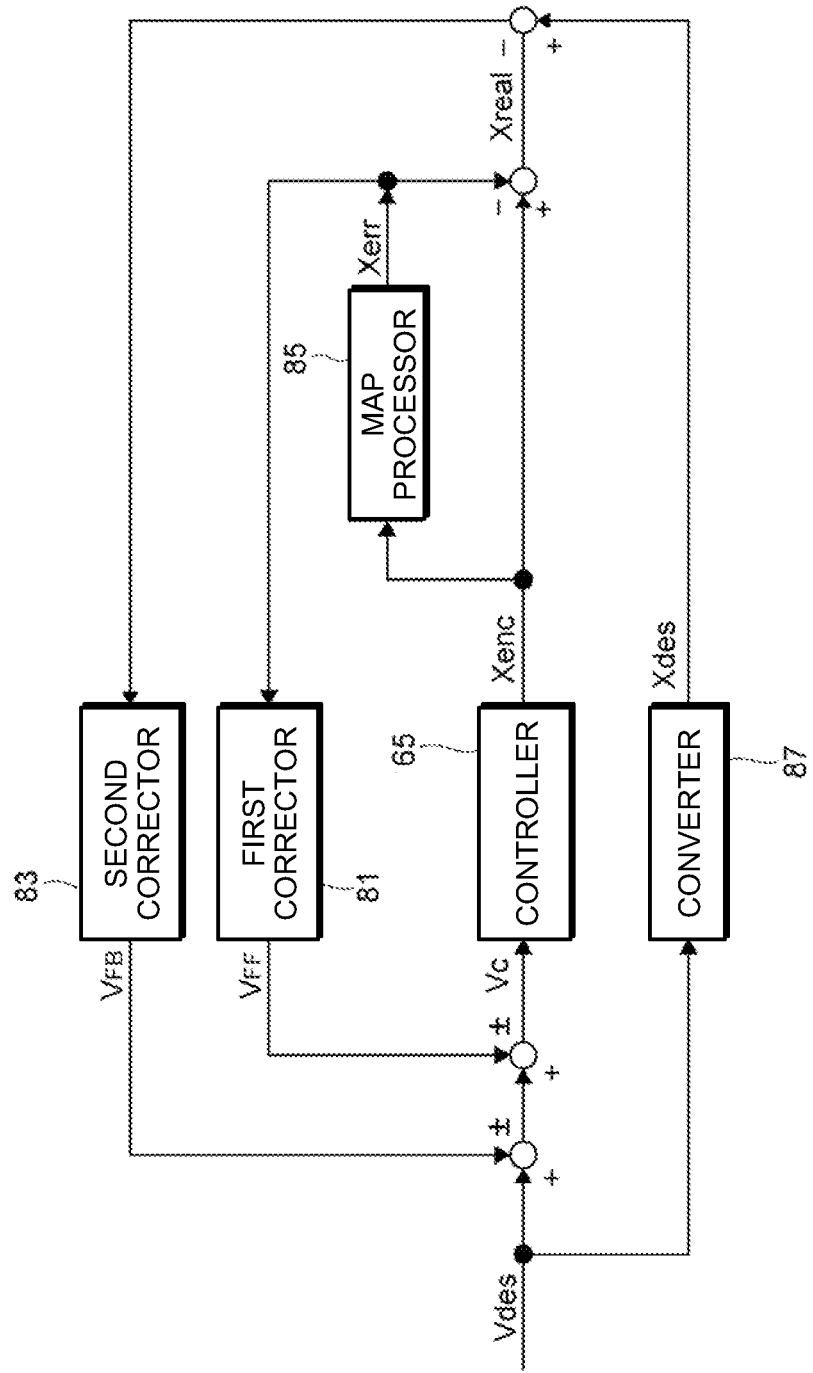
FIG. 10 is a control block diagram illustrating the contents of processing by a first control method.

FIG. 10 is a control block diagram illustrating the contents of processing by the first control method. The speed setting value Vdes is corrected by feedforward control using a speed correction value VFF from a first corrector 81, which will be described later in detail, and by feedback control using a speed correction value VFB from a second corrector 83, which will be described later in detail, and signals of the speed correction value Vc resulting from the correction is input to the controller 65.

The controller 65 drives the pulse motor 73 illustrated in FIG. 8 based on the input signals of the speed correction value Vc. As a result, the rod 51 serving as the movable part moves with the ball screw shaft 71 and the nut 69. The controller 65 outputs a present position Xenc of the movable part obtained by the position sensor 67 detecting the movement of the rod 51.

The present position Xenc output from the controller 65 is input to a map processor 85. The map processor 85 includes the correction amount map in which the lead error and the error due to cogging, which are the errors measurable in advance, are mapped for each position of the movable part. The map processor 85 refers to the correction amount map and outputs a position correction amount Xerr corresponding to the present position Xenc.

The position correction amount Xerr is input to the first corrector 81. The first corrector 81 performs correction processing on the speed setting value Vdes by the position correction amount Xerr corresponding to the error amount known to occur in advance. In other words, the first corrector 81 calculates the speed correction value VFF for adjusting the speed setting value Vdes such that the error indicated by the position correction amount Xerr is 0. In other words, the first corrector 81 adjusts the speed setting value Vdes based on the position correction amount Xerr by feedforward control.

The speed setting value Vdes input to the controller 65 is also input to a converter 87. The converter 87 estimates an ideal movement position Xdes of the movable part when the actuator is driven based on the input speed setting value Vdes.

Subsequently, a corrected present position Xreal is calculated by correcting the present position Xenc of the movable part output from the controller 65 by the position correction amount Xerr corresponding to the present position Xenc. The second corrector 83 adjusts the speed setting value Vdes such that the calculated corrected present position Xreal approaches the ideal movement position Xdes. In other words, the second corrector 83 outputs the speed correction value VFB for correcting the speed setting value Vdes and adjusts the speed setting value Vdes so as to reduce the difference between the corrected present position Xreal and the ideal movement position Xdes.

In other words, the second corrector 83 performs correction on the errors unmeasurable in advance, such as thermal expansion and abrasion of the ball screw device. This correction is performed by adjusting the speed setting value Vdes by feedback control such that there is no difference between the corrected present position Xreal and the ideal movement position Xdes.

The correction amount in the second corrector 83 is reduced because the correction processing in the second corrector 83 is performed on the corrected present position Xreal obtained by correcting the errors measurable in advance by the first corrector 81 as the correction target. As a result, the correction processing can be performed with a small gain, thereby making excessive adjustment, such as overshooting and hunting, less likely to occur, and the speed setting value Vdes can be adjusted with high accuracy.

Either the correction of the speed setting value Vdes using the speed correction value VFF by the first corrector 81 or the correction using the speed correction value VFB by the second corrector 83 may be performed first.

<Second Control Method>

The following describes a second control method. The first control method secures the accuracy of each shaft in the axial direction. The actuator, however, moves back and forth not only in the axial direction but also while making pitching and yawing motions (moves back and forth while swinging vertically and horizontally). For this reason, the movement cannot be corrected by the first control method based on a single axis. In addition, errors cannot be detected by the position sensor 67 because they are not the errors in the axial direction. Therefore, errors caused by pitching and yawing motions need to be corrected by other axes.

To address this, the second control method integrates positional information on five axes and performs control. The following describes a procedure for determining, in a multi-axis parallel link robot obtained by integrating a plurality of the driving devices 10, the command signals to be supplied to each of the driving devices 10 to move the end effector to a desired target position and posture.

Figure 11:
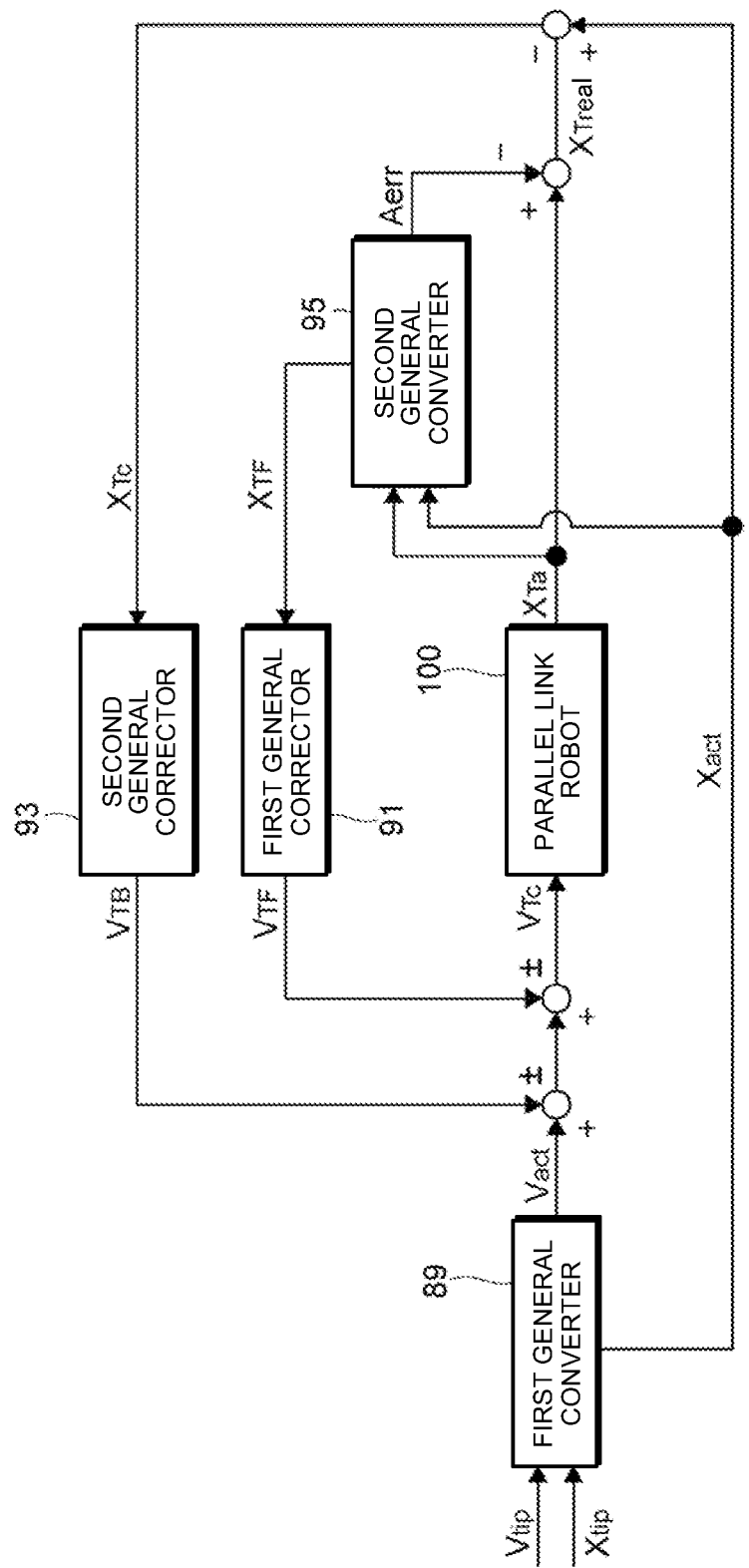
FIG. 11 is a control block diagram illustrating the contents of processing by a second control method.

FIG. 11 is a control block diagram illustrating the contents of processing by the second control method. The command signals Sd indicate a tip position Xtip and a needle tip speed Vtip of the needle 25 in the end effector 21 illustrated in FIG. 1. When receiving the signals of the tip position Xtip and the needle tip speed Vtip, a first general converter 89 calculates a speed setting value Vact of the movable part of each of the driving devices 10 based on the received signals. The speed setting value Vact is represented as a five-dimensional matrix because it is used for control on the five-axis parallel link robot 100.

The speed setting value Vact is corrected to a corrected speed setting value $V_{Tc}$ of a five-dimensional matrix by a speed correction value $V_{TF}$ from a first general corrector 91 and a speed correction value $V_{TB}$ from a second general corrector 93, which will be described later, and the corrected speed setting value is input to each of the driving devices 10 of the parallel link robot 100.

Each of the driving devices 10 of the parallel link robot 100 drives the actuator in accordance with the corresponding speed setting value based on the input corrected speed setting value $V_{Tc}$ and outputs the present position of the movable part detected by the position sensor 67 (FIG. 8). The parallel link robot 100 integrates present positions $X_{Ta}$ of the movable parts of the respective driving devices 10 and outputs the integrated positions as a five-dimensional matrix.

Figure 12:
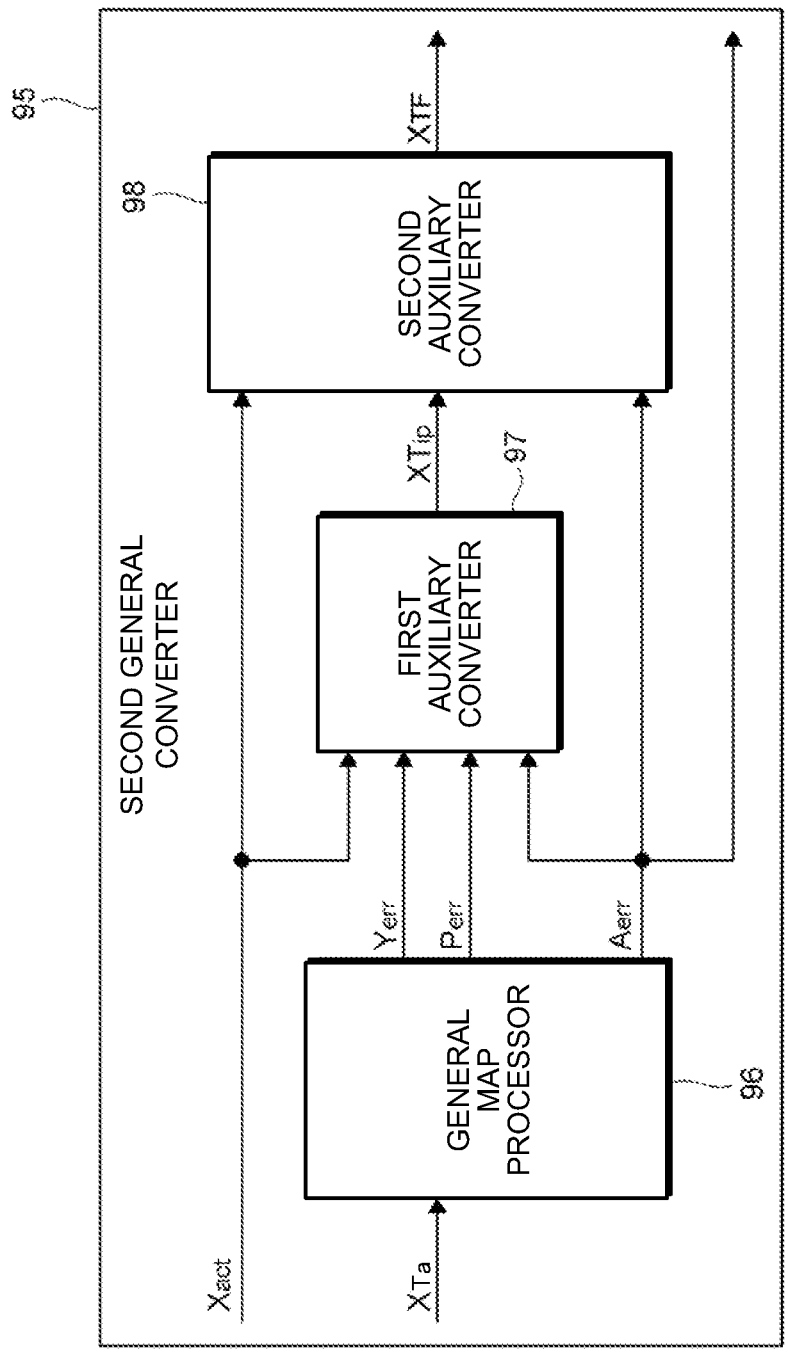
FIG. 12 is a control block diagram of a second general converter.

The information on the present position $X_{Ta}$ is input to a second general converter 95. FIG. 12 is a control block diagram of the second general converter 95. The signal of the present position $X_{Ta}$ of each of the driving devices 10 is input to a general map processor 96. The general map processor 96 has a correction amount map in which an error Yerr in the yawing direction, an error Perr in the pitching direction, and an error Aerr in the axial direction, which are the errors measurable in advance described above, in each of the driving devices 10 are mapped for each position.

The general map processor 96 refers to the correction amount map and outputs, to a first auxiliary converter 97, the error Yerr in the yawing direction, the error Perr in the pitching direction, and the error Aerr in the axial direction in each of the driving devices 10 based on the received present position $X_{Ta}$ of the movable part of each of the driving devices 10.

The first auxiliary converter 97 receives the errors Yerr, Perr, and Aerr and information on a target position Xact output from the first general converter 89 (FIG. 11). The first auxiliary converter 97 predicts an error of the tip position of the needle 25 in the end effector 21 from the input information and outputs an error amount XTip to a second auxiliary converter 98.

The second auxiliary converter 98 receives the error amount XTip, the target position Xact output from the first general converter 89, and the error Aerr in the axial direction output from the general map processor 96. The second auxiliary converter 98 outputs a feedforward control amount $X_{TF}$ of each of the driving devices 10 based on the input information.

The feedforward control amount $X_{TF}$ is input to the first general corrector 91 illustrated in FIG. 11. The first general corrector 91 calculates a speed correction value $V_{TF}$ corresponding to the input feedforward control amount $X_{TF}$ and corrects the speed setting value Vact output from the first general converter 89.

A corrected present position $X_{Treal}$ is calculated by correcting the present position $X_{Ta}$ of the movable part output from the parallel link robot 100 by using the error Aerr in the axial direction corresponding to the present position $X_{Ta}$. The second general corrector 93 adjusts the speed setting value Vact such that the corrected present position $X_{Treal}$ becomes close to the target position Xact serving as a target. In other words, the second general corrector 93 outputs a speed correction value $V_{TB}$ for correcting the speed setting value Vact and adjusts the speed setting value Vact so as to reduce a difference $X_{Tc}$ between the corrected present position $S_{Treal}$ obtained by correcting the present position $X_{Ta}$ by using the error Aerr in the axial direction and the target position Xact.

Even when the actuator moves back and forth while making pitching and yawing motions, this configuration can correct the effects of the movement by using the other axes and perform highly accurate control.

As described above, the parallel link robot 100 with this configuration can obtain the accurate position of the distal end (needle tip) of the end effector 21 by each of the driving devices 10 obtaining the position of the distal end of the movable part. Therefore, the parallel link robot 100 can control the posture of the end effector using any desired point on the axis of the end effector 21 as the center of rotation by independently controlling the individual driving devices 10, for example. In other words, the parallel link robot 100 can accurately and stably perform remote center of motion (RCM) control for causing the robot to move around a point at a remote position from the driving device 10.

The present invention is not limited to the embodiment described above. Combinations of the components according to the embodiment and modifications and applications by those skilled in the art based on the description in the specification and known technologies are also included in the present invention and falls within the scope of protection sought.

While the embodiment above describes an example where the present invention is applied to an ophthalmic surgical robot including a plurality of driving devices, the application example is not limited thereto. The present invention can be suitably applied to various kinds of robots, such as medical and drug-developing robots and processing robots, that require high accuracy in position of the distal end of an end effector, for example.

As described above, the following items are disclosed in the present specification.

(1) A driving device comprising a corrector configured to correct a command signal that is input and generate a correction signal, an actuator configured to move a movable part forward and backward based on the correction signal, and a position sensor configured to detect a present position of the movable part, wherein the actuator comprises a nut connected to the movable part, a ball screw shaft onto which the nut is screwed, and a pulse motor configured to drive to rotate the ball screw shaft, the corrector includes a correction amount map in which a position correction amount for calibrating a predictable error due to a structure of the actuator is mapped for each position of the movable part, the corrector estimates an ideal movement position to which the movable part moves based on the command signal, the corrector refers to the correction amount map and calculates the position correction amount corresponding to the present position detected by the position sensor, and the corrector generates the correction signal by correcting the command signal so as to reduce a difference between a corrected present position obtained by correcting the present position by the position correction amount and the ideal movement position. The driving device corrects the input command signal using the correction amount map for the predictable error due to the structure of the actuator and then performs correction so as to reduce the difference between the corrected present position and the ideal movement position. Therefore, the driving device can reduce the correction amount in the latter correction processing. Thus, the correction processing can be performed with a smaller gain, and high positional accuracy can be stably achieved.

(2) The driving device according to (1), wherein the predictable error includes at least one of a lead error of the ball screw shaft or a rotation error due to cogging of the pulse motor. The driving device can correct the lead error and the rotation error due to cogging.

(3) The driving device according to (1) or (2), wherein the position sensor is a linear encoder. The driving device can directly detect movement of the movable part along the movement direction and can perform highly accurate detection.

(4) The driving device according to any one of (1) to (3), wherein the pulse motor is a stepping motor. The driving device has higher stability when stationary and has a simpler configuration because it does not require a rotary encoder to detect rotation. In addition, the driving device can be driven by constant voltage, maintain a stationary state when the power supply is turned off, and stably maintain the posture of the robot.

(5) A method for controlling a driving device comprising a corrector configured to correct a command signal that is input and generate a correction signal, an actuator configured to move a movable part forward and backward based on the correction signal, and a position sensor configured to detect a present position of the movable part, wherein the actuator comprises a nut connected to the movable part, a ball screw shaft onto which the nut is screwed, and a pulse motor configured to drive to rotate the ball screw shaft, the corrector includes a correction amount map in which a position correction amount for calibrating a predictable error due to a structure of the actuator is mapped for each position of the movable part, and the method comprises: estimating an ideal movement position to which the movable part moves based on the command signal; referring to the correction amount map and calculating the position correction amount corresponding to the present position detected by the position sensor; and generating the correction signal by correcting the command signal so as to reduce a difference between a corrected present position obtained by correcting the present position by the position correction amount and the ideal movement position. According to the method for controlling the driving device, the input command signal is corrected using the correction amount map for the predictable error due to the structure of the actuator, and then correction is performed so as to reduce the difference between the corrected present position and the ideal movement position. Therefore, the correction amount in the latter correction processing can be reduced. Thus, the correction processing can be performed with a smaller gain, and high positional accuracy can be stably achieved.

(6) A parallel link robot comprising a plurality of driving devices each comprising a corrector configured to correct a command signal that is input and generate a correction signal, an actuator configured to move a movable part forward and backward based on the correction signal, and a position sensor configured to detect a present position of the movable part, the parallel link robot being configured to change a position and a posture of a robot distal end shaft, wherein the actuator comprises a nut connected to the movable part, a ball screw shaft onto which the nut is screwed, and a pulse motor configured to drive to rotate the ball screw shaft, the corrector includes a correction amount map in which a position correction amount for calibrating a predictable error due to a structure of the actuator is mapped for each position of the movable part, the corrector estimates an ideal movement position to which the movable part moves based on the command signal, the corrector refers to the correction amount map and calculates the position correction amount corresponding to the present position detected by the position sensor, and the corrector generates the correction signal by correcting the command signal so as to reduce a difference between a corrected present position obtained by correcting the present position by the position correction amount and the ideal movement position. The parallel link robot can accurately control the speed and the position of the distal end of the movable part by the independent control device of each linkage, thereby reliably determining the speed and the position of the distal end shaft. By driving the pulse motor based on the correction signal, the speed and the position of the robot distal end shaft can be finely adjusted, thereby enabling the robot to be stably stationary and driven.

(7) The parallel link robot according to (6), wherein the driving devices comprises: a first driving device and a second driving device disposed with directions of movement of the movable parts parallel to each other; a first connection member to which the movable part of the first driving device and the movable part of the second driving device are connected in a manner separated from each other, the first connection member being capable of tilting by movement of the movable parts; a third driving device and a fourth driving device provided to the first connection member and disposed with directions of movement of the movable parts parallel to each other; a second connection member to which the movable part of the third driving device and the movable part of the fourth driving device are connected in a manner separated from each other, the second connection member being capable of tilting by movement of the movable parts; and a fifth driving device provided to the second connection member, and a tilt axis of the first connection member, a tilt axis of the second connection member, and a movement axis of the movable part of the fifth driving device are orthogonal to one another. The parallel link robot can perform orthogonal five-axis drive control with high positional accuracy and high stability.

(8) The parallel link robot according to (7), wherein an end effector is provided to the robot distal end shaft. The parallel link robot can position the end effector with high accuracy.

(9) The parallel link robot according to (8), wherein the end effector is provided with an ophthalmic surgical instrument. The parallel link robot can be driven with high accuracy and high stability.

(10) A method for controlling a parallel link robot comprising a plurality of driving devices each comprising a corrector configured to correct a command signal that is input and generate a correction signal, an actuator configured to move a movable part forward and backward based on the correction signal, and a position sensor configured to detect a present position of the movable part, the parallel link robot being configured to change a position and a posture of a robot distal end shaft, wherein the actuator comprises a nut connected to the movable part, a ball screw shaft onto which the nut is screwed, and a pulse motor configured to drive to rotate the ball screw shaft, the corrector includes a correction amount map in which a position correction amount for calibrating a predictable error due to a structure of the actuator is mapped for each position of the movable part, and the method comprises: estimating an ideal movement position to which the movable part moves based on the command signal; referring to the correction amount map and calculating the position correction amount corresponding to the present position detected by the position sensor; and generating the correction signal by correcting the command signal so as to reduce a difference between a corrected present position obtained by correcting the present position by the position correction amount and the ideal movement position. According to the method for controlling the parallel link robot, the speed and the position of the distal end of the movable part can be accurately controlled by the independent control device of each linkage, thereby reliably determining the speed and the position of the distal end shaft. By driving the pulse motor based on the correction signal, the speed and the position of the robot distal end shaft can be finely adjusted, thereby enabling the robot to be stably stationary and driven.

The invention claimed is:

1. A parallel link robot comprising a plurality of driving devices each including an actuator configured to move a movable part forward and backward, the parallel link robot being configured to change a position and a posture of a robot distal end shaft, wherein
the actuator comprises a nut connected to the movable part, a ball screw shaft onto which the nut is screwed, and a pulse motor configured to drive to rotate the ball screw shaft,
the driving devices comprises:
a first driving device and a second driving device disposed with directions of movement of the movable parts parallel to each other;
a first connection member to which the movable part of the first driving device and the movable part of the second driving device are connected in a manner separated from each other, the first connection member being capable of tilting by movement of the movable parts;
a third driving device and a fourth driving device provided to the first connection member and disposed with directions of movement of the movable parts parallel to each other;
a second connection member to which the movable part of the third driving device and the movable part of the fourth driving device are connected in a manner separated from each other, the second connection member being capable of tilting by movement of the movable parts; and
a fifth driving device provided to the second connection member, and
a tilt axis of the first connection member, a tilt axis of the second connection member, and a movement axis of the movable part of the fifth driving device are orthogonal to one another.

2. The parallel link robot according to claim 1, wherein an end effector is provided to the robot distal end shaft.

3. The parallel link robot according to claim 2, wherein the end effector is provided with an ophthalmic surgical instrument.

4. A method for controlling a parallel link robot comprising a plurality of driving devices each comprising a corrector configured to correct a command signal that is input and generate a correction signal, an actuator configured to move a movable part forward and backward based on the correction signal, and a position sensor configured to detect a present position of the movable part, the parallel link robot being configured to change a position and a posture of a robot distal end shaft, wherein
the actuator comprises a nut connected to the movable part, a ball screw shaft onto which the nut is screwed, and a pulse motor configured to drive to rotate the ball screw shaft,
the corrector includes a correction amount map in which a position correction amount for calibrating a predictable error due to a structure of the actuator is mapped for each position of the movable part,
the driving devices comprises:
a first driving device and a second driving device disposed with directions of movement of the movable parts parallel to each other;
a first connection member to which the movable part of the first driving device and the movable part of the second driving device are connected in a manner separated from each other, the first connection member being capable of tilting by movement of the movable parts;
a third driving device and a fourth driving device provided to the first connection member and disposed with directions of movement of the movable parts parallel to each other;
a second connection member to which the movable part of the third driving device and the movable part of the fourth driving device are connected in a manner separated from each other, the second connection member being capable of tilting by movement of the movable parts; and
a fifth driving device provided to the second connection member, and
a tilt axis of the first connection member, a tilt axis of the second connection member, and a movement axis of the movable part of the fifth driving device are orthogonal to one another, and
the method comprises:
estimating an ideal movement position to which the movable part moves based on the command signal;

referring to the correction amount map and calculating the position correction amount corresponding to the present position detected by the position sensor; and generating the correction signal by correcting the command signal so as to reduce a difference between a corrected present position obtained by correcting the present position by the position correction amount and the ideal movement position.

\* \* \* \* \*